United States Patent [19]

Lin et al.

[11] Patent Number: 4,525,979

[45] Date of Patent: Jul. 2, 1985

[54] AUTOMATIC BOTTLE SEALING MECHANISM FOR LIQUID SAMPLING APPARATUS

[75] Inventors: Philip C. Lin; James S. Ho, both of Cincinnati, Ohio

[73] Assignee: The United States of America as represented by the Administrator of the Environmental Protection Agency, Washington, D.C.

[21] Appl. No.: 435,169

[22] Filed: Oct. 19, 1982

[51] Int. Cl.³ .......................... B65B 3/06; B65B 7/16
[52] U.S. Cl. ...................................... 53/268; 53/285;
53/376; 215/315; 141/350; 141/326
[58] Field of Search ................ 53/281, 285, 283, 376,
53/290, 329, 474, 468, 274, 268, 238; 215/315,
342, 322; 141/326, 330, 334, 350

[56] References Cited

U.S. PATENT DOCUMENTS

| | | | |
|---|---|---|---|
| 316,147 | 4/1885 | Heysinger | 215/315 X |
| 1,623,775 | 4/1927 | Blanchard | 141/350 |
| 2,578,201 | 12/1951 | Nicorvo | 215/315 |
| 3,179,132 | 4/1965 | Focht | 141/350 X |
| 3,792,803 | 2/1974 | Kessler | 215/315 X |

*Primary Examiner*—Horace M. Culver

[57] ABSTRACT

An automatic bottle sealing mechanism is provided for use with an automatic liquid sampling apparatus of the type having a plurality of sample receiving bottles and a movable sample distributing spout for sequentially filling the bottles with liquid samples. The bottle sealing mechanism includes a cap body adapted to be fitted over the mouth of a sample bottle in place of the usual screw cap or other type of closure. The cap body includes an open throat for allowing liquids to be poured into the sample bottle, a movable closure member for opening and closing the cap body throat, and a spring loaded latch mechanism for automatically moving the closure member to a closed position in response to the movement of the sample distributing spout. The invention promptly and automatically seals the sample receiving bottles after they are filled with a liquid sample, thereby preventing the evaporative loss of volatile substances contained in the liquid samples while obviating the need for subsequent manual sealing of the bottles. In one embodiment, the closure member carries a sharpened lance or spike for puncturing a preservative container housed in the cap body, which allows a perservative liquid to be automatically added to the liquid sample immediately after the sample receiving bottle is sealed.

15 Claims, 11 Drawing Figures

AUTOMATIC BOTTLE SEALING MECHANISM FOR LIQUID SAMPLING APPARATUS

BACKGROUND OF THE INVENTION

1. Field of the Invention

The invention generally relates to an automatic sealing device for containers, and is specifically concerned with an automatic sealing mechanism for sample receiving bottles of the type used in automatic liquid sampling devices.

2. Description of the Prior Art

In order to effectively monitor the water quality in a flowing river or stream, or to measure pollutant levels in industrial waste effluents which are discharged into natural bodies of water, it is generally necessary to take successive water samples at regular intervals over a period of time which typically ranges between twenty-four to forty-eight hours. It is possible to carry out the sampling procedure manually, with the samples either being tested in the field as soon as they are obtained or accumulated for testing at a later time, but in either case manual sampling becomes tedious and cumbersome when a large number of samples must be taken over a long period of time. For this reason, automatic sampling devices have been developed which are capable of obtaining and storing a number of liquid samples at regular intervals without human supervision. At the end of the sampling period, the bottled samples can all be retrieved and tested at the same time, thereby avoiding many of the manipulative difficulties involved in manual sampling.

A typical automatic liquid sampling apparatus of the type available at the present time is illustrated in FIG. 1. The apparatus consists of a thermally insulated bottom casing section 20 for holding a circular array of sample receiving bottles 22 (shown with caps 23 in place), a thermally insulated upper casing section 24 which fits over the lower casing section 20, and a protective upper cover 26. A circular wall 28 is spaced inwardly from the outer wall of the lower casing section 20 to provide an annular space for receiving and locating the bottles 22. The central area inside the inner wall 28 provides a space for ice to be stored for preserving the liquid samples after they have been introduced into the bottles 22. A watertight electrical control unit 30 and a peristaltic pump 32 are affixed to the upper casing section 24, the latter serving to draw in liquid samples through an intake device 34 and a flexible tube 36. The output of the pump 32 is connected by additional lengths of flexible tubing 38 and 39 to a rotating sample distributing spout 40 mounted on the underside of the upper casing section 24. The sample distributing spout 40 is rotated over the mouths of the bottles 22, from which the caps 23 are first removed, in an incremental or step-by-step manner. This is accomplished by a motor (not shown) under the control of the control unit 30. The pump 32 is also controlled by the control unit 30 and is operated during the stationary intervals of the spout 40. In this way, each of the bottles 22 is filled in sequence with a liquid sample delivered by the spout 40. Typically, the control unit 30 can be programmed so that samples are taken according to a preset time schedule, as for example once every sixty minutes. Alternatively, sampling may occur at intervals corresponding to a certain amount of volumetric flow of the effluent from which samples are being taken, as measured by an external flow sensing device. Although each discrete liquid sample will usually be introduced into a separate one of the bottles 22, the control unit 30 can in some instances be programmed to fill two or more of the bottles 22 during each sampling cycle, or conversely, to combine two or more successive liquid samples in each bottle.

Although automatic liquid sampling devices of the type shown in FIG. 1 have proved very useful in eliminating much of the time-consuming field work involved in obtaining water samples at remote locations, certain difficulties still remain. A particularly troublesome problem involves the uncapping and recapping of the sample receiving bottles 22. When the automatic sampling apparatus is set up for operation at the location where the samples are to be taken, the caps 23 must be removed from the bottles 22 so that the latter can be filled in sequence by the sample distributing spout 40. When the sampling period has ended, and all of the bottles 22 have been filled, the caps 23 must usually be replaced in order to allow the bottles to be transported to a laboratory or other testing site without spillage of the liquid samples. Aside from the manipulative difficulty involved in separately recapping each of the numerous bottles contained in the sampling apparatus, there is the additional problem that the bottles have remained uncapped, with their contents exposed to the surrounding air, for a substantial amount of time before the end of the sampling period. For example, during a typical automatic sampling operation in which a total of twenty-four bottles are filled and a one-hour interval is provided between successive sampling cycles, the first bottle to be filled will remain uncapped for about twenty-four hours before the sampling operation is completed, even if the bottles are retrieved and sealed immediately. This presents problems in cases where the liquid being sampled is drinking water or waste water containing volatile organic compounds. Commonly occurring examples of such compounds include carbon tetrachloride, 1,1,2-trichloroethylene, and 1,1,2,2-tetrachloroethylene. The delay between filling and sealing of the bottles can allow these compounds to escape by evaporation, thereby reducing the accuracy and validity of subsequent testing procedures. In addition, the surrounding air can sometimes contaminate or oxidize the substances present in liquid samples if the sample receiving bottles are left open for an excessive length of time.

Recent studies have suggested that water samples containing volatile organic compounds can be preserved intact for relatively long periods of time, in some cases up to eight to ten days, if the sample bottles are sealed promptly after filling with a minimum of air space between the liquid sample and the bottle cap. Unfortunately, presently available types of automatic liquid sampling devices, such as that shown in FIG. 1, do not provide any means for sealing the sample receiving bottles until the automatic sampling operation is complete and all of the bottles have been filled, and even then the bottles must be sealed manually. Prior to the present invention, the only known way to avoid the delay in sealing the sample receiving bottles was to interrupt the automatic sampling operation after each bottle was filled, manually place a cap on that particular bottle, resume the automatic sampling operation, and then repeat the process for each of the remaining bottles. The obvious disadvantage of this procedure is that it requires constant human supervision and intervention, thereby offsetting most of the advantages to be gained from the use of the automatic sampling apparatus.

SUMMARY OF THE INVENTION

The invention obviates the aforementioned disadvantages associated with the prior art by providing an automatic bottle sealing mechanism which promptly and automatically seals the sample bottles. In its broadest aspect, the invention includes a cap body having a throat for receiving a sample substance and conducting it through the mouth of a bottle, a movable closure member capable of opening and closing the throat in the cap body, and an actuating means which automatically moves the closure means so that it opens or closes the throat in the cap body.

The cap body of the invention is adapted to be fitted over the mouth of the sample receiving bottle. The movable closure member may include a vane which is slidable from an open position to a closed position across the throat in the cap body. The actuating means preferably includes a means for storing potential energy which is connected to the slidable vane of the closure member, and a latch means for releasing this energy so that the vane slides into a closed position.

The slidable vane comprising the movable closure member may be located below the top opening of the throat in order to reduce the amount of air trapped in the closed bottle. The potential energy storing means of the latch may include any device capable of storing energy, but is preferably a mechanical spring which is connected at one end to the slidable vane. This spring may be placed in a state of compression when the slidable vane is in the open position. The latch means may also include a rotatable trip rod which automatically releases the spring whenever the spout of an automatic sampling device engages and rotates the trip rod into a particular position, thereby sliding the vane into the closed position.

The cap body of the invention may be horizontally elongated, and may terminate at one end in a wall having a slot into which the trip rod is receivable. The trip rod may be mechanically connected to the same end of the spring to which the slidable vane is connected by means of a connecting hook, so that the vane slides into a closed position whenever the spout of an automatic sampling device rotates the trip rod into alignment with the slot. Finally, the other end of the horizontally elongated cap body may include a puncturable container filled with a fluid perservative for preserving the substances in the sample fluid when the slidable vane closes the sample bottle. A lance for puncturing the container of preservative may be mechanically connected to the slidable vane so that the lance punctures the container when the vane slides into the closed position, thereby releasing the fluid preservative into the sample fluid.

BRIEF DESCRIPTION OF THE DRAWINGS

The various objects, advantages and novel features of the invention will be more readily apprehended from the following detailed description when read in conjunction with the appended drawings, in which.

Throughout the drawings, like reference numerals will be used to refer to like parts.

DETAILED DESCRIPTION OF THE PREFERRED EMBODIMENTS

Figure 1:
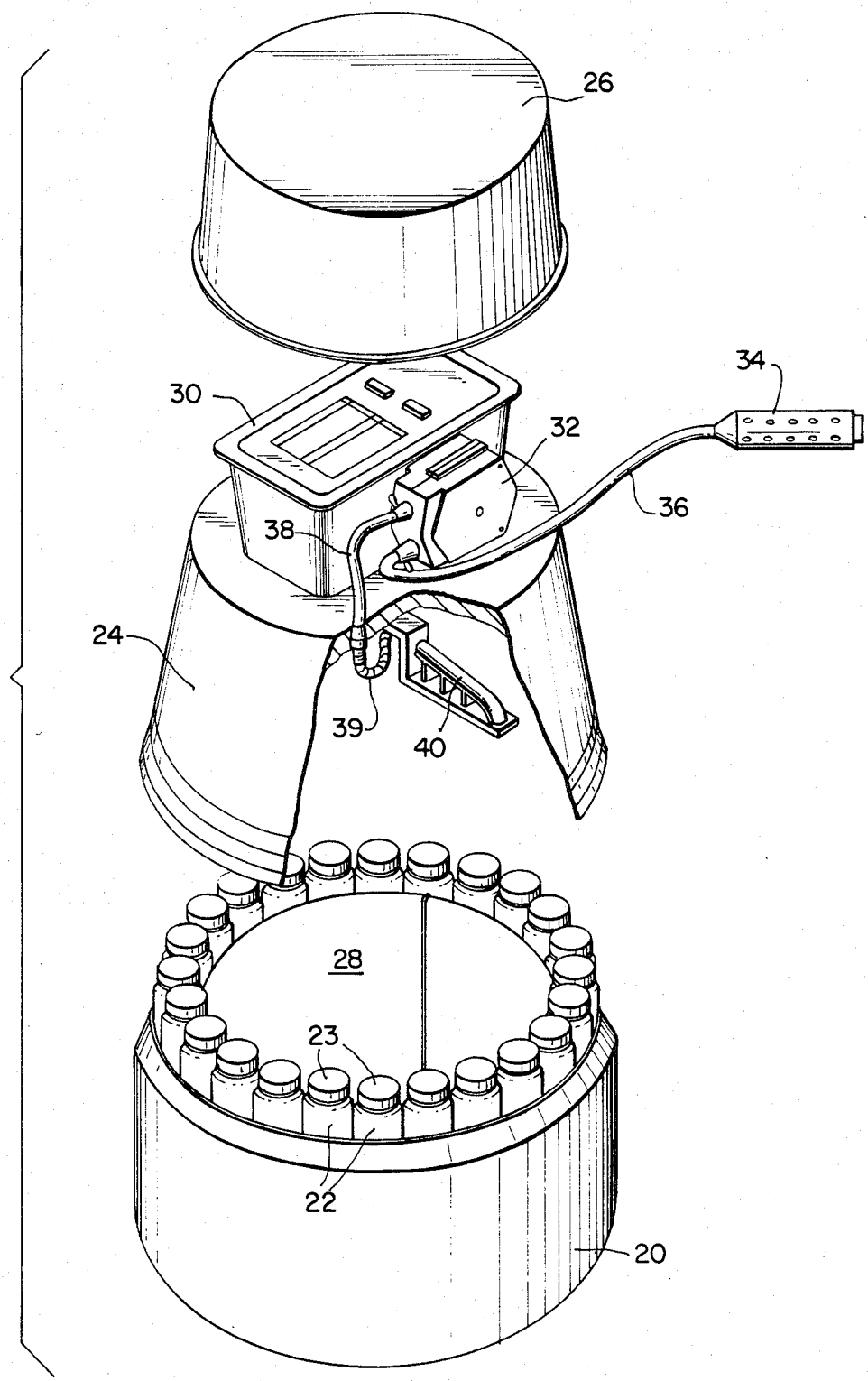
FIG. 1, previously described, is an exploded perspective view of a typical automatic liquid sampling apparatus with which the present invention can be employed.

A first embodiment of an automatic bottle sealing mechanism constructed in accordance with the present invention is illustrated in FIGS. 2–5. The device includes a cap body 42 which is adapted to be fitted over the mouth of a sample receiving bottle (not shown) in place of the usual screw cap or other type of closure. The cap body 42 includes a main body portion 44, which is generally in the shape of a rectangular block with a circular bottom flange 45 and a rounded end surface 46, and a frusto-conical end portion 48 attached to the main body portion 44 on the side opposite the rounded end surface 46. The main body portion 44 is provided with an externally threaded portion 50 for engaging internal screw threads formed within the open inner end 52 of the frusto-conical end portion 48, thereby allowing the two parts 44 and 48 of the cap body 42 to be coupled together. When so coupled, the cap body 42 is provided with a horizontally elongated shape, as shown, having the rounded surface 46 at one end thereof and the narrow part of the frusto-conical portion 48 at the opposite end thereof.

Figure 2:
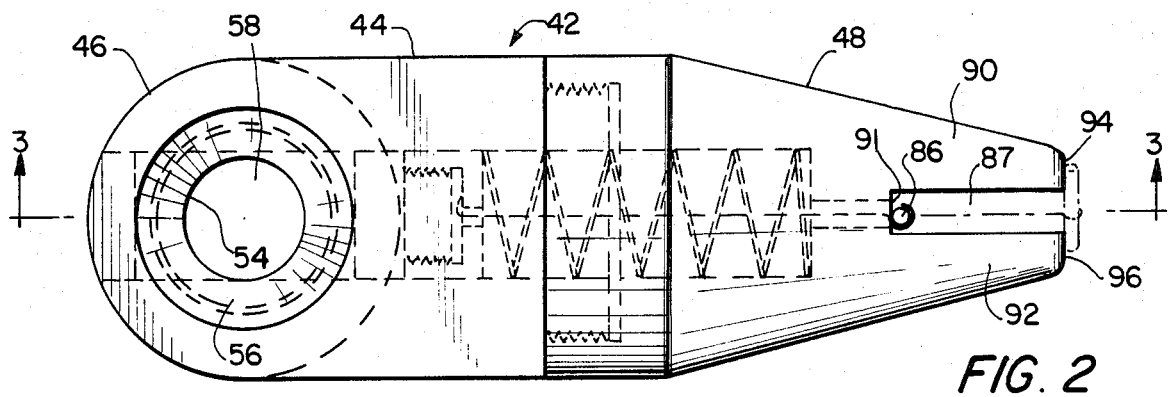
FIG. 2 is a top plan view of a first embodiment of the invention.
Figure 3:
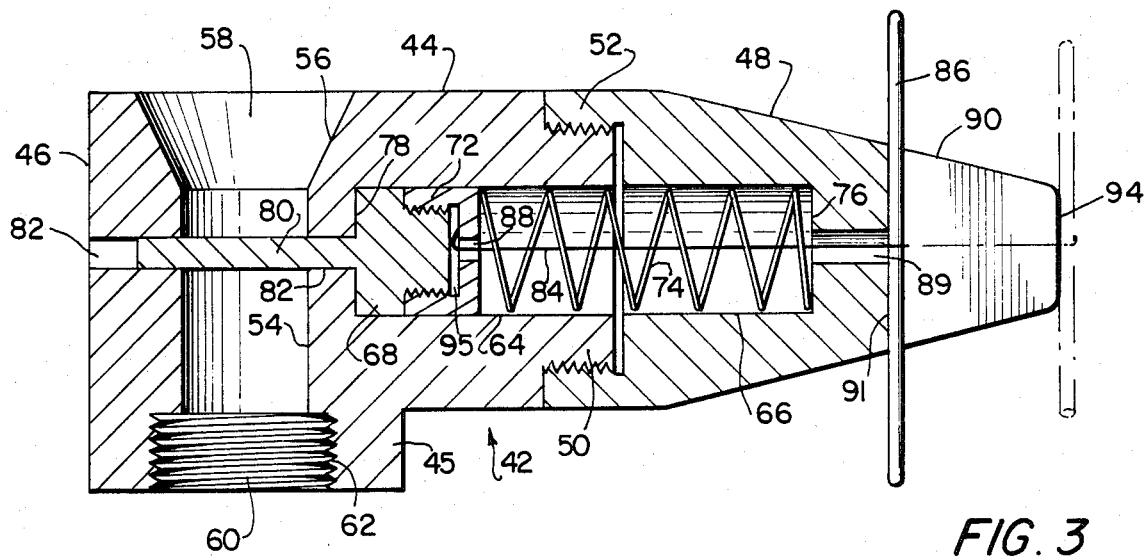
FIG. 3 is a side sectional view of the first embodiment of the invention, taken along the line 3—3 in FIG. 2.

The main body portion 44 of the cap body 42 is formed with an open vertical throat 54, best illustrated in FIGS. 2 and 3, which serves as a fluid conduit for allowing liquid samples to be poured through the cap body and into a suitable sampling receiving bottle. The upper portion of the throat 54 has outwardly flared or inclined side walls 56, as shown, to serve as a pouring funnel for the liquid samples. The upper portion 56 of the throat 54 terminates in a top opening or inlet 58 through which the liquid samples are introduced. The bottom portion of the throat 54 terminates in an outlet opening 60 which allows the liquids to pass into an attached sample receiving bottle (not shown). Internal screw threads 62 are provided within the bottom opening 60 of the throat 54 in order to allow the cap body 42 as a whole to be fitted and sealed over the mouth of the sample receiving bottle. Of course, the screw threads 62 may be replaced with other suitable types of fastening means, if necessary, depending upon the type of closure cap that is normally used with the sample receiving bottle.

Figure 5:
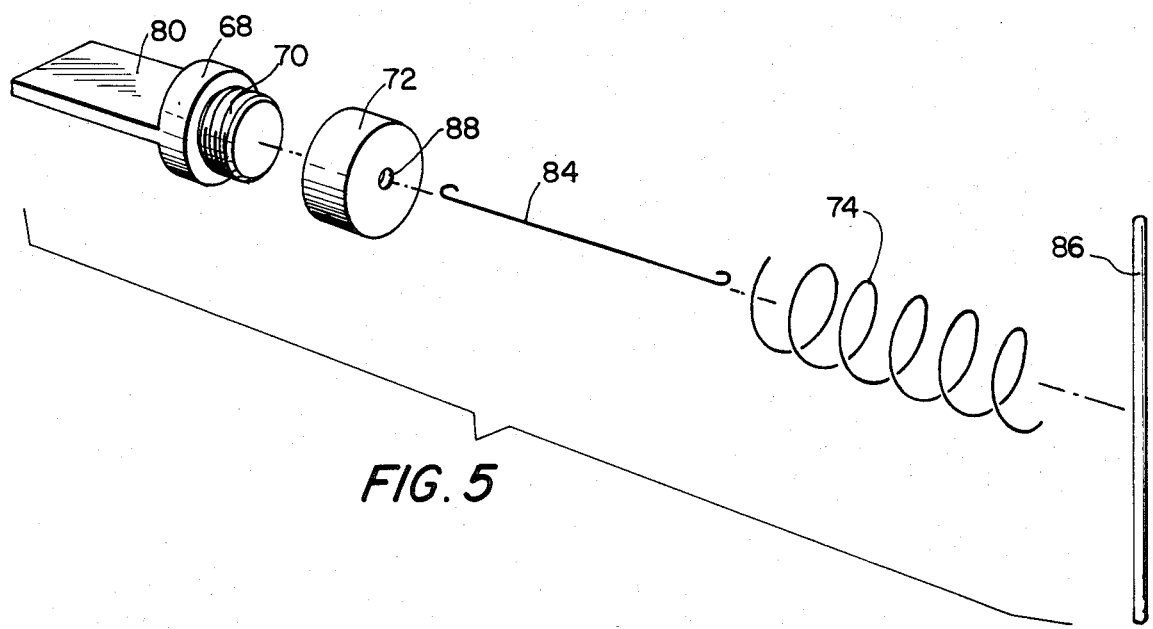
FIG. 5 is an exploded perspective view of the internal components of the embodiment of FIGS. 2–4.

The main body portion 44 and frusto-conical end portion of the cap body 42 are formed with open cylindrical cavities 64 and 66, respectively, which are placed in alignment with each other when the two parts 44 and 48 of the cap body are coupled together, as illustrated in FIG. 3. A movable closure member 68, whose configuration will be most easily appreciated from the exploded perspective view of FIG. 5, is positioned in the left-hand end of the cavity 64 as shown in FIG. 3. One end of the closure member 68 is provided with external screw threads 70 for engaging an internally threaded retaining cap 72. A coil spring 74 is enclosed by the aligned cavities 64 and 66 and is maintained in compression between the outer face of the retaining cap 72 and the opposite vertical end wall 76 of the cavity 66. The closure member 68 is horizontally slidable within the aligned cavities 64 and 66, but is normally maintained in abutting contact with the vertical end wall 78 of the cavity 64 as a result of the compressive force exerted by the spring 74.

As best seen in FIGS. 3 and 5, the closure member 68 is provided with a flat closure vane 80. The closure vane 80 is slidably received in a horizontal slot 82 which intersects the vertical throat 54 of the main body portion 44 of the cap body 42. The slot 82 has a width which is at least equal to, and is preferably slightly greater than, the diameter of the throat 54 at the point where it is intersected by the slot. The slot 82 extends horizontally in the left-hand direction and opens onto the curved end surface 46 of the main body portion 44 of the cap body 42. The slot 82 also extends horizontally in the right-hand direction and communicates with the cylindrical cavity 64, in which the main portion of the closure member 68 is received. The width of the closure vane 80 is at least equal to, and is preferably slightly greater than, the diameter of the throat 54 at the point where the throat is intersected by the horizontal slot 82. Thus it will be appreciated that, as the closure member 68 slides back and forth within the aligned cavities 64 and 66 under the influence of the spring 74, the depending closure vane 80 will move across the throat 54 to provide an opening and closing function therein. In the closed position of the vane, which is the position shown in FIGS. 2 and 3, the vane 80 extends completely across the cross-section of the throat 54 and forms a closure seal between the top opening 58 and bottom opening 60 of the cap body. In this position of the vane, therefore, a sample receiving bottle attached to the bottom opening 60 of the cap body will be effectively sealed and evaporation or spillage of its contents will be prevented. Initial filling of the sample receiving bottle is possible by sliding the closure member 68 in the right-hand direction, as viewed in FIGS. 2 and 3, against the compressive force exerted by the spring 74. This will cause the closure vane 80 to move to an open position in which the vane is completely withdrawn from the interior of the throat 54, thus allowing liquids to pass freely from the top opening 58 of the cap body to the bottom opening 60.

In accordance with an important feature of the present invention, a latch arrangement is provided for allowing the closure member 68 to operate automatically once it has been installed in a conventional type of automatic liquid sampling apparatus. This arrangement includes, in addition to the spring 74, an elongated metal hook 84, a vertically positioned trip rod 86, and a vertical slot 87 formed in the narrow end portion of the frusto-conical part 48 of the cap body 42 for slidably receiving the trip rod 86. The vertical slot 87 is defined between a pair of horizontally extending members 90 and 92 which are arranged in a side-by-side relationship with each other, with each of the members 90 and 92 extending from and integrally formed with the frusto-conical portion 48 of the cap body 42 at the narrow end thereof. The hook 84 is curved or bent at each end, as shown, with one end engaging a small hole 88 formed through the end face of the retaining cap 72. This serves to connect the hook 84 to the closure member 68 for movement therewith. The opposite end of the hook 84 passes through a small horizontal clearance hole 89 formed in the frusto-conical portion 48 of the cap body 42 between the cavity 66 and the slot 87, and is bent partially around the trip rod 86 at an intermediate point thereon.

It will be appreciated that the upstanding trip bar 86, which projects above and below the respective upper and lower surfaces of the frusto-conical portion 48 of the cap body 42 as shown in FIG. 3, can be grasped manually by its upper and lower ends and caused to slide in the right-hand direction until it has moved past the right-hand end of the slot 87. The trip rod 64 will remain substantially vertical during such movement as a result of being confined between the interior side walls of the vertical slot 87. The horizontal sliding motion of the trip rod 86 will be transmitted by the hook 84 and retaining cap 72 to the closure member 68, causing the closure member to move to the right within the cavities 64 and 66 and also causing the spring 74 to be further compressed. As a result of this motion, the closure vane 80 slides to the right within the horizontal slot 82, eventually reaching the open position in which the vertical throat 54 of the cap body 42 is open and unobstructed. At this point, the trip rod 86 has cleared the slot 87 and can be rotated slightly about a horizontal axis defined by the axis of the elongated hook 84. This causes a slight twisting of the elongated hook 84, which is accommodated at its left-hand end by a small gap 95 provided between the interior wall of the retaining cap 72 and the right-hand end of the closure member 68. The rotation of the trip rod 68 will cause it to move out of alignment with the vertical slot 87 and to bridge across the right-hand end of the slot. When the trip rod is then released, it will be brought into contact with, and will rest against, the flat end faces 94 and 96 of the members 90 and 92, thereby assuming the cocked or latched position indicated in phantom lines in FIGS. 2–4. The restoring force exerted by the spring 74, acting through the retaining cap 72 and elongated hook 84, will force the median portion of the latch rod 86 into firmly abutting contact with the flat end surfaces 94 and 96 of the members 90 and 92, thereby maintaining the trip rod in the cocked or latched position. As long as the trip rod 86 remains in this position, the closure vane 80 will be arrested in its open or withdrawn position and the throat 54 will remain open to allow liquids to pass from the top opening 58 of the cap body to the bottom opening 60.

Figure 4:
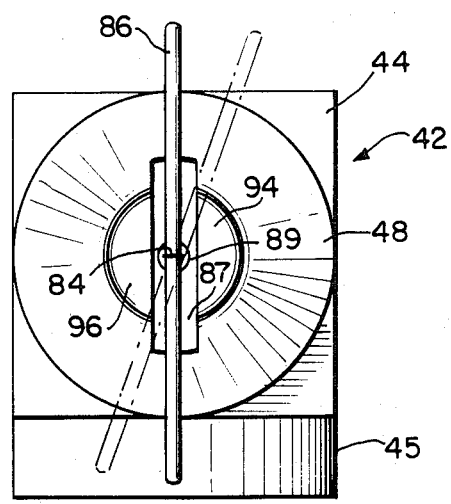
FIG. 4 is an end view of a first embodiment of the invention, viewed from the right-hand side in FIG. 3.

When the cocked or latched trip rod 86 is acted upon by an external force in a direction tending to realign the trip rod with the vertical slot 87, the trip rod will be rapidly pulled back into the slot 87 and moved inward to the limit of its travel, defined by the back wall 91 of the slot 87, due to the restoring force of the spring 74 acting through the retaining cap 72 and the elongated hook 84. With reference to FIG. 4, in which the cocked or latched position of the trip rod is shown in phantom, this would occur as a result of a force acting in the left-hand direction on the upper portion of the trip rod or, equivalently, as a result of a force acting in the right-hand direction on the lower portion of the trip rod. In either case, the trip rod 86 is restored to its fully vertical position and is then completely retracted into the slot 87 as noted previously. The retracted position of the trip rod 86 within the confines of the slot 87 is referred to as its tripped position, this position being shown in solid outlines in FIGS. 2-4. The movement of the trip rod 68 to this position is accompanied by movement of the closure member 68 to the closed position due to the restoring force exerted by the compressed spring 74. Therefore, when the trip rod 86 moves to the tripped position, the closure vane 80 is fully inserted into the horizontal slot 82 and the vertical throat 54 of the cap body is completely closed.

It will be appreciated from the foregoing description that the spring 74 serves as a means for storing potential energy, which energy is used to operate the closure member 68. Energy is required to move the closure member 68 from the closed position to the open position, since movement of the closure member in this direction involves overcoming the restoring force exerted by the spring 74. This energy is stored in the spring 74 while the latter is maintained in a compressed condition, which corresponds to the interval during which the trip rod 86 is maintained in its cocked or latched position. When the trip rod 86 is tripped by an external force as described previously, the energy stored in the spring 74 is released and is used to move the closure member 68 to the closed position, while simultaneously carrying the trip rod 86 to its tripped position. It will be apparent that the spring 74 may be replaced with other types of mechanical or electrical devices capable of storing and releasing energy, although the spring 74 is preferred because of its simplicity and reliability. It will also be apparent that the spring 74 and its associated components may be rearranged, if desired, to operate in tension rather than in compression.

Various modifications may be made to the embodiment of FIGS. 2-5 without departing from the scope of the invention, such as the substitution of a different type of closure member or the relocation of the closure member to a different point in the vertical throat 54. In this connection it should be noted that it is desirable to locate the closure member at a point well below the top opening 58 of the cap body 42 in order to minimize the trapped air space over the liquid sample when the closure is in the closed position. This objective is met in the illustrated embodiment by locating the closure vane 80 at an intermediate point between the top opening 58 of the cap body 42 and the bottom opening 60. This location is advantageous for the additional reason that it places the closure vane 80 in a protected position within the throat 54, so that its operation will not be obstructed or impaired by objects which may inadvertently come into contact with the top surface of the cap body 42.

Figure 6:
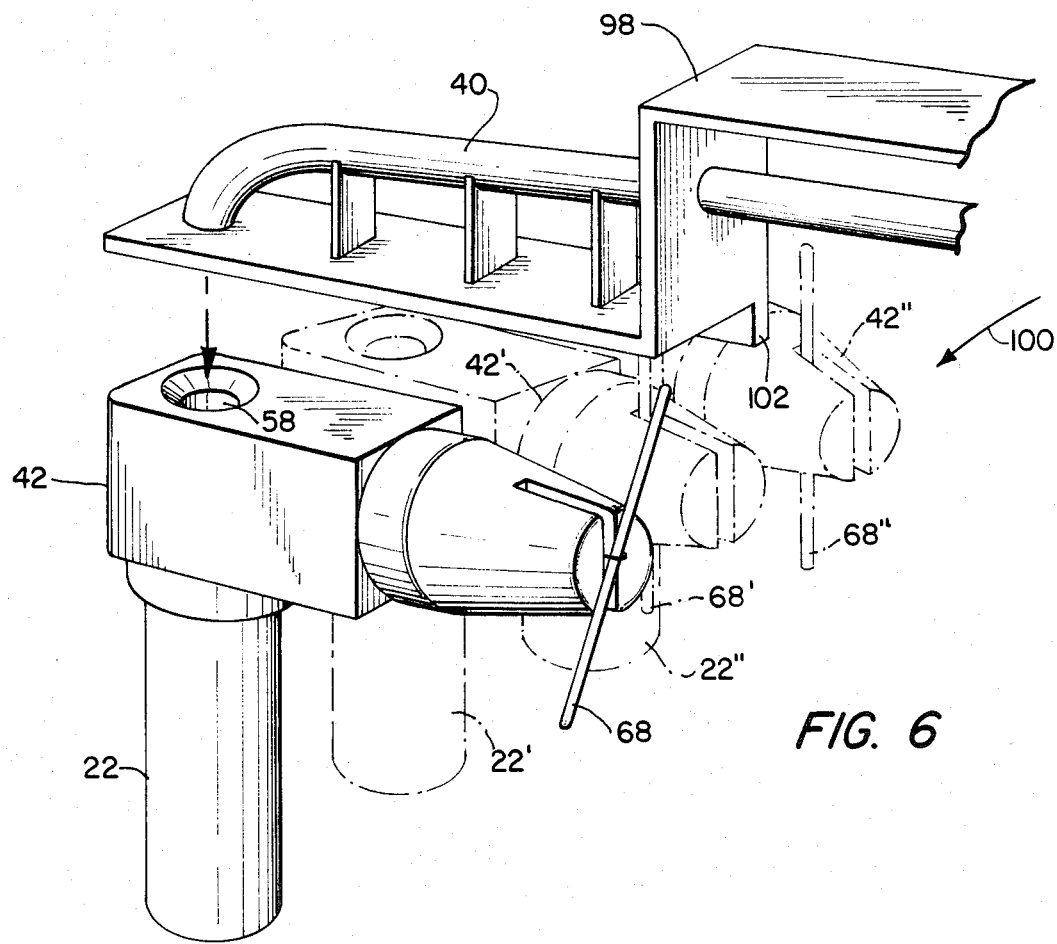
FIG. 6 is a perspective view illustrating the manner in which the first embodiment of the invention is employed in an automatic liquid sampling apparatus.
Figure 7:
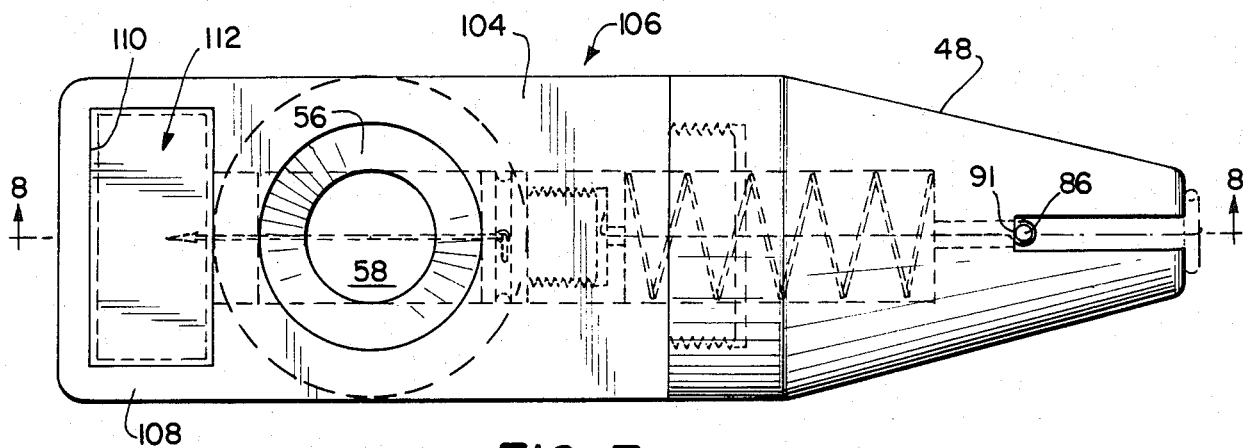
FIG. 7 is a top plan view of a second embodiment of the invention.

FIG. 6 is a perspective view illustrating the manner in which the invention may be employed in connection with a conventional type of automatic liquid sampling apparatus. A cap body 42 of the type described in FIGS. 2-5 is shown attached to a sample receiving bottle 22, it being understood that the mouth of the bottle 22 will normally be provided with screw threads which can be engaged with the screw threads 62 provided in the bottom opening of the cap body (FIG. 3).

The sample receiving bottle 22 is positioned next to two other sample receiving bottles 22' and 22", each being fitted with a cap body 42' and 42" identical in all respect to the cap body 42. The bottles 22, 22' and 22" will normally be arranged with numerous additional bottles in a circular array within the bottom section of an automatic sampling apparatus as illustrated in FIG. 1. The movable sample distributing spout 40, which is also illustrated in FIG. 1, is supported by a frame 98 for intermittent rotational movement as described earlier. For purposes of illustration, such movement will be assumed to occur in a counterclockwise direction as indicated by the arrow 100. In order to adapt the automatic sampling apparatus for use with the present invention, the underside of the spout frame 98 is provided with a downwardly-extending lip or projection 102, which is at the proper height to make contact with the trip rods 68, 68' 68" when the latter are in their cocked or latched positions. The position of the lip or projection 102 is also such that it does not touch the cocked trip rod 68 of a particular bottle 22 until after that bottle has been filled with a liquid sample and the spout 40 has begun to move toward the next bottle. Thus in FIG. 6, the cap body 42 of the sample receiving bottle 22 which is being filled by the spout 40 has its trip rod 68 in the cocked position, whereas the trip rods 68' and 68" of the cap bodies 42' and 42" associated with the previous two bottles 22' and 22" have already been moved to their tripped positions since these bottles have already been filled. The operation of most automatic samplers is such that, as soon as a given bottle has been filled with a liquid sample, the sample distributing spout begins to move to the next bottle and then remains poised over the next bottle until the preset interval between sampling cycles has expired. This mode of operation is desirable from the standpoint of the present invention, since it means that the latch rod 68 associated with each bottle will be tripped to seal the bottle almost immediately after the bottle has been filled, rather than after a delay interval equal to the interval between successive sampling cycles. However, even if the opposite mode of operation is employed, wherein the stationary interval of the spout 40 occurs over the bottle which has already been filled rather than over the next bottle to be filled, the delay in sealing each bottle will still be no more than the interval between successive sampling cycles. This is a great improvement over the prior art technique in which the bottles 22 could normally be sealed only after the completion of the entire sampling operation, that is, after the last bottle has been filled.

The completely mechanical operation of the automatic bottle sealing mechanism of FIGS. 2-6 is advantageous since it permits the device to be used at remote locations where electric power may be unavailable. The automatic sampling machines with which the invention is intended to be used are generally designed to be powered either by conventional line current or by auxiliary storage batteries, but during battery-powered operation it is important to avoid excessive drain on the storage batteries. Therefore, although electrically-operated embodiments of the present invention are possible, the completely mechanical embodiment described above will be preferable in most situations.

A modified embodiment of the present invention is illustrated in FIGS. 7-10. This embodiment is in most respects the same as the embodiment of FIGS. 2-5, and parts which are essentially identical in both embodiments have been correspondingly numbered in the drawings. In the modified embodiment, however, the main body portion 104 of the cap body 106 is provided with an integral extension 108 on the side of the throat 54 opposite the frusto-conical portion 48. The extension 108 is provided with a rectangular cavity 110, having an opening on the top surface of the main body portion 104, for receiving a close-fitting preservative container 112. The preservative container 112 may comprise a rigid outer carton or box 114 made of plastic or cardboard, and a thin inner liner 116 made of plastic or cellophane film, or some other material which can be easily punctured. A preservative liquid 118 is contained within the inner liner 116 as shown. The outer carton 114 of the preservative container is provided with a circular hole 120, best seen in the exploded view of FIG. 10, which is approximately aligned with a horizontal fluid passage 122 when the container 112 is in position within the rectangular cavity 110. The fluid passage 122 communicates between the cavity 110 and the vertical throat 54 of the main body portion 104. The purpose of the fluid passage 122 is to allow the preservative liquid 118 to drip from the container 112 into a sample receiving bottle attached to the bottom opening 60 of the cap body 106, as will be explained hereinafter.

Figure 8:
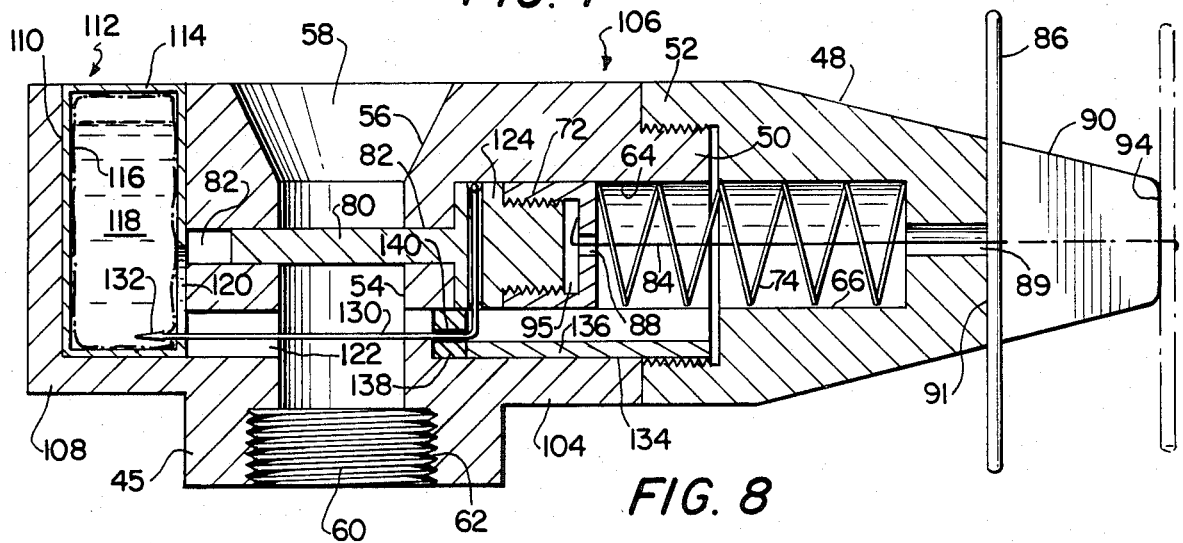
FIG. 8 is a side sectional view of the second embodiment of the invention, taken along the line 8—8 in FIG. 7.
Figure 9:
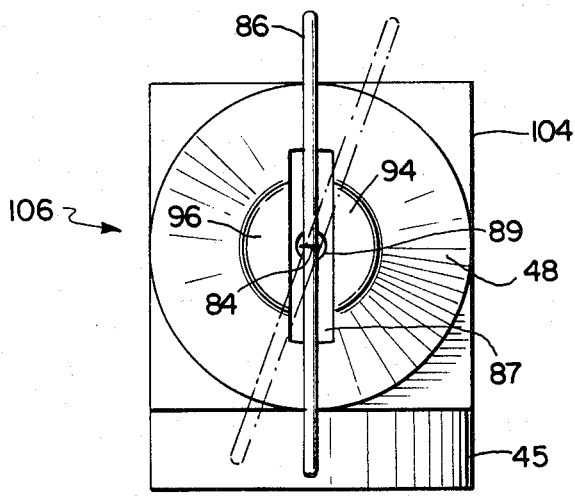
FIG. 9 is an end view of the second embodiment of the invention, viewed from the right-hand side in FIG. 8.
Figure 10:
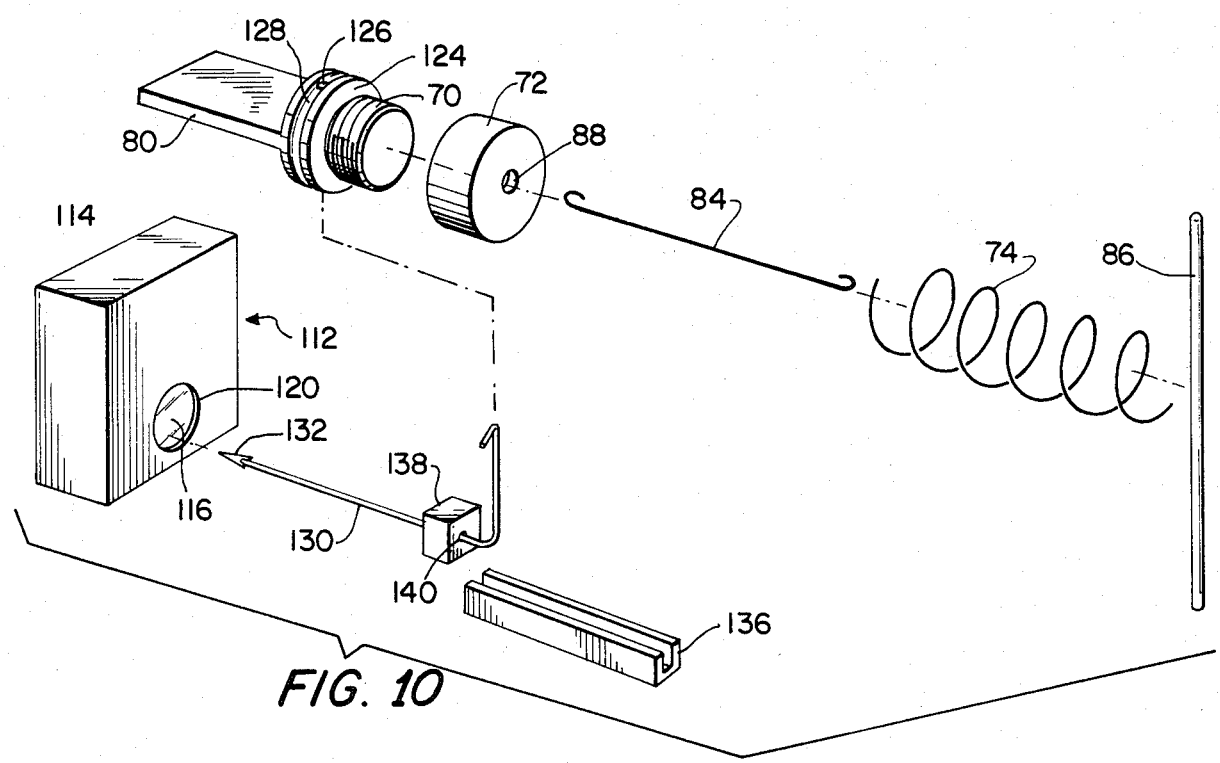
FIG. 10 is an exploded perspective view of the internal components of the embodiment of FIGS. 7–9.

As can be seen most clearly in FIGS. 8 and 10, the proximal portion of the movable closure member 124 is provided with a transverse through-hole 126 and a peripheral groove 128 for receiving the vertical portion of an L-shaped lance or spike 130. The L-shaped lance 130 may be made from a length of rigid metal wire or the like and is provided with a sharpened tip 132. An interior groove or slot 134 is formed longitudinally within the main body portion 104 of the cap body 106 adjacent to and below the cavity 64, for the purpose of receiving an elongated U-shaped channel member 136. The channel member 136 serves as a guide for the lower horizontal portion of the lance or spike 130 as the latter moves back and forth as a consequence of the movement of the closure member 124. A sealing block 138 is provided at the end of the channel member 136 closest to the throat 54 of the cap body 106. The sealing block 138 contains a small through-hole 140 in which the lower horizontal portion of the lance 130 is slidably received. The sealing block 138 prevents the infiltration of liquids from the throat 54 into the cavities 64 and 66 which enclose the spring 74 and the other components associated with the slidable closure member 124. The through-hole 140 is aligned with a further hole 142 formed through the vertical side wall of the throat 54 for allowing the lance 130 to pass into the throat 54 and through the fluid passage 122 as shown.

The operation of the modified embodiment of FIGS. 7-10 is substantially the same as the operation of the earlier embodiment, although the modified embodiment provides the additional function of introducing a liquid preservative into the sample receiving bottle immediately after the bottle is sealed by the closure vane 80. Thus with reference to FIG. 8, it can be seen that as the closure member 124 is moved in the left-hand direction toward the closed position under the influence of the spring 74, the lance 130 will be moved an equal distance across the throat 54 and through the fluid passage 122. As the closure vane 80 reaches its fully closed position within the horizontal slot 82, the sharpened tip 132 is thrust through the hole 120 in the carton 114 of preservative container 112 and ruptures or punctures the inner line 116. This allows the preservative liquid 118 to escape through the fluid passage 122 and to drain into the sample receiving bottle through the bottom opening 60 of the cap body 106. It should be observed that, due to the close fit between the preservative container 112 and the rectangular cavity 110 in which it is received, the sample receiving bottle will be effectively sealed off from outside air when the closure vane 80 is in the fully closed position as shown. If desired, however, an additional sealing cap can be provided over the top opening of the cavity 110 to prevent any infiltration of air or liquid vapors through the cavity 110 and fluid passage 122.

Figure 11:
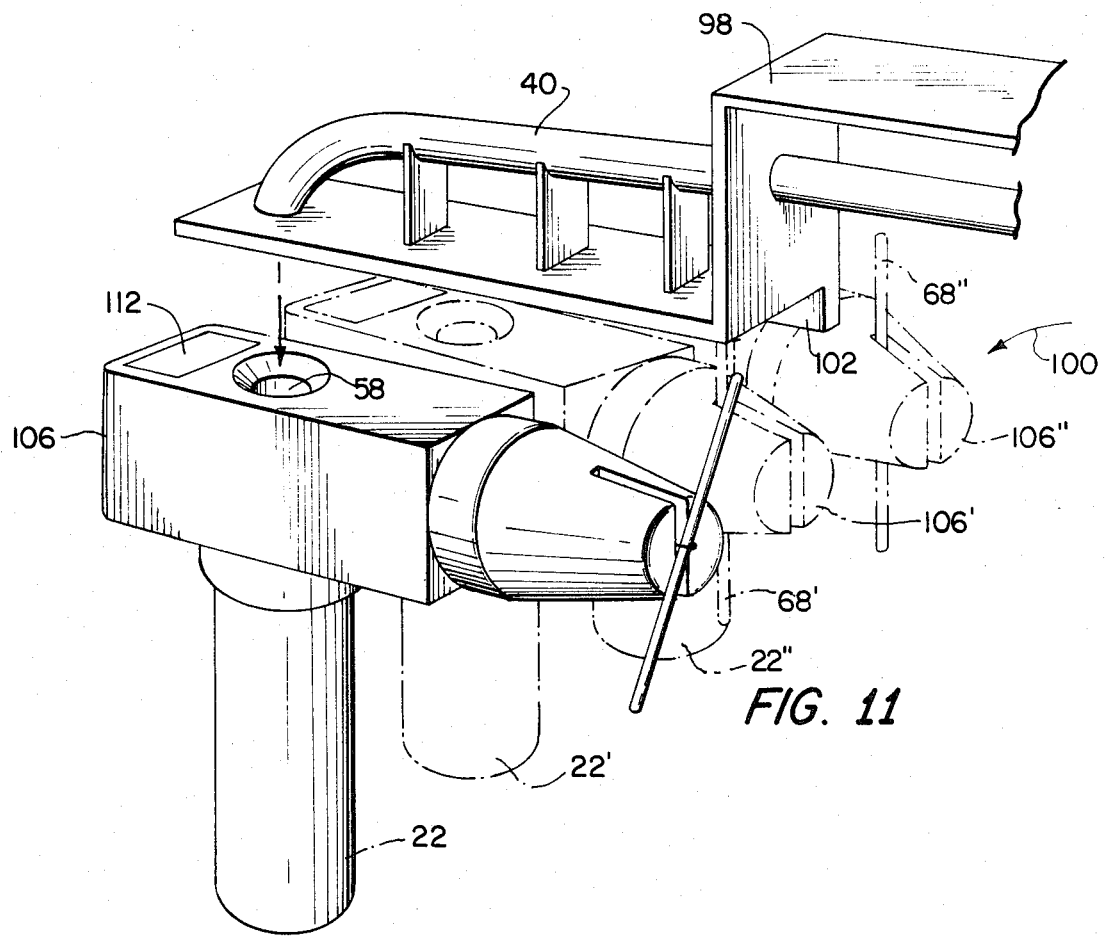
FIG. 11 is a perspective view illustrating the manner in which the second embodiment of the invention is employed in an automatic liquid sampling apparatus.

FIG. 11 illustrates the manner in which automatic bottle sealing devices of the type illustrated in FIGS. 7-10 can be fitted over the sample receiving bottles 22 of an automatic liquid sampling apparatus. As described earlier in connection with FIG. 6, the tripping of the trip rods 68 by the lip 102 on the lower part of the spout frame 98 causes the bottles 22 to be sealed automatically after they have been filled with liquid samples. In this case, however, a preservative liquid is introduced into each of the sample receiving bottles 22 from the preservative containers 112 at the same time as the bottles 22 are sealed. This is advantageous in instances where the liquid samples contain components which are reactive with each other in the sealed sample receiving bottle. Unless a preservative is added to inhibit the reaction, it is difficult to obtain meaningful test results unless the samples are analyzed immediately. For example, certain types of organic contaminants found in drinking water are reactive with residual chlorine which may also be present in the water. The addition of a suitable preservative, such as a solution of sodium thiosulfide, will inhibit the reaction and preserve the liquid sample long enough for the organic contaminants to be readily detected and measured.

The various components of the automatic bottle sealing devices of FIGS. 2-6 and 7-11, with the exception of metal components such as the spacing 74, hook 84 and lance 130, are preferably made from a suitable plastic material which is inert to the pollutants and contaminants typically found in the liquid samples of interest. Teflon is a suitable plastic material for this purpose.

Although the present invention has been described with reference to a preferred embodiment, the invention is not limited to the details thereof. A number of possible modifications and substitutions have been suggested in the foregoing detailed description, and others will occur to those of ordinary skill in the art. All such substitutions and modifications are intended to fall within the scope of the invention as defined in the appended claims.

What is claimed is:

1. A bottle sealing mechanism for automatically sealing a bottle comprising:
    (a) a cap body adapted to be fitted over the mouth of said bottle, said body including a throat for receiving a substance and conducting it through the mouth of said bottle, said throat including a top opening for receiving a substance and a bottom opening for delivering said substance to said bottle;
    (b) a movable closure member capable of moving into an open position, wherein said throat is open, and a closed position, wherein said throat is closed, said movable closure member including a slidable vane which is slidable across said throat between said top opening and said bottom opening and selectively moveable to an open throat or a closed throat position, and (c) an actuating means for automatically moving said closure member from said open position to said closed position, including:
  (i) a potential energy storing means connected to said movable closure member capable of moving said closure member from an open position to a closed position when said energy is released, said potential energy storing means including a spring having one end in contact with said slidable vane and being in a state of compression when the vane is in said open throat position, and
  (ii) a latch means for releasing the potential energy stored in said storing means, said latch means including a trip rod which is mechanically connected to said one end of the spring by means of a connecting hook.

2. The bottle sealing mechanism defined in claim 1, wherein said cap body includes a wall having a slot, and wherein said trip rod is rotationally movable over said wall and receivable into said slot, and wherein said slidable vane slides into said closed position when said trip rod is aligned with said slot.

3. A bottle sealing mechanism for automatically sealing a bottle, comprising:
  (a) a cap body adapted to be fitted over the mouth of said bottle, said body including a throat for receiving a substance and conducting it through the mouth of said bottle;
  (b) a movable closure member capable of moving into an open position, wherein said throat is open, and a closed position, wherein said throat is closed, and
  (c) an actuating means for automatically moving said closure member from said open position to said closed position, including:
    (i) a potential energy storing means connected to said movable closure member capable of moving said closure member from an open position to a closed position when said energy is released,
    (ii) a latch means for releasing said potential energy, and
    (iii) means for automatically tripping said latch means in response to the movement of a sample distributing spout which sequentially introduces fluid samples into a plurality of said bottles.

4. The bottle sealing mechanism defined in claim 3, wherein said movable closure member includes a slidable vane.

5. The bottle sealing mechanism defined in claim 4, wherein said throat includes an upper opening and a lower opening, and wherein said vane is slidable across said throat between said upper opening and said lower opening.

6. The bottle sealing mechanism defined in claim 5, wherein said actuating means includes a rotatable trip rod, and wherein said slidable vane slides into said closed position when said spout engages said trip rod and rotates it into a predetermined position.

7. The bottle sealing mechanism defined in claim 6, wherein said source of potential energy includes a spring having one end in contact with said slidable vane.

8. The bottle sealing mechanism defined in claim 7, wherein said spring is in a state of compression when said slidable vane is in said open position.

9. The bottle sealing mechanism defined in claim 8, wherein said trip rod is mechanically connected to said one end of the spring by means of a connecting hook, whereby said trip rod is biased toward said throat.

10. The bottle sealing mechanism defined in claim 9, wherein said cap body includes a wall having a slot, and wherein said trip rod is rotationally movable over said wall and receivable into said slot, and wherein said slidable vane moves into said closed position whenever said spout engages and rotates said trip rod so that it is aligned with said slot.

11. The automatic bottle sealing mechanism defined in claim 10 wherein said cap body includes a puncturable container containing a fluid preservative, and a lance member connected to said slidable vane for puncturing said puncturable container when said vane slides into a closed position, whereby said fluid preservative flows into said bottle.

12. An automatic bottle sealing mechanism for use with an automatic liquid sealing apparatus having a plurality of sample receiving bottles and a movable sample distributing spout for sequentially introducing liquid samples into said sample receiving bottles, comprising:
  (a) a cap body adapted to be fitted over the mouth of a sample receiving bottle, said cap body having a top opening into which liquids can be poured, a bottom opening for communicating with the interior of the sample receiving bottle, and an open throat between said top opening and said bottom opening,
  (b) movable closure means provided in said cap body for closing off said open throat, said closure means being movable between an open position in which said throat is open to permit liquids to be poured into the sample receiving bottle, and a closed position in which said throat is closed to liquids and the sample receiving bottle is effectively sealed,
  (c) latch means connected to said closure means and effective when engaged to maintain said closure means in the open position, and when disengaged to move said closure means to the closed position, said latch means comprising:
    (i) a trip member adapted to be positioned in the path of the movable sample distributing spout of an automatic liquid sampling apparatus and to be tripped thereby in order to disengage said latch means, and
    (ii) potential energy storing means for storing energy produced by movement of the closure means from the closed position to the open position, and for releasing said stored energy to return the closure means to the closed position when the latch means is disengaged by the tripping of the trip member.

13. An automatic bottle sealing mechanism as claimed in claim 12, wherein said movable closure means includes a substantially flat closure vane which is movable across the open throat of the cap body, said flat closure vane being slidably received in a slot which opens into the side wall of said throat.

14. An automatic bottle sealing mechanism as claimed in claim 13, wherein said cap body has a horizontally elongated shape with said open throat occupying a position near one end thereof, the opposite end of said cap body being provided with a pair of horizontally extending members arranged in side-by-side relationship with each other and defining an open vertical slot therebetween, and wherein said trip member comprises an elongated trip rod positioned vertically in said vertical slot and arranged for horizontal sliding movement within said vertical slot while remaining substantially in said vertical position.

15. An automatic bottle sealing mechanism as claimed in claim 14, wherein said cap body includes a puncturable container which contains a preservative, and a lance connected to said sliding vane for puncturing said puncturable container when said vane is moved into said closed position, whereby said preservative is released into the mouth of said bottle.

* * * * *